United States Patent [19]

Kataoka et al.

[11] Patent Number: 5,973,069
[45] Date of Patent: Oct. 26, 1999

[54] POLYETHYLENE OXIDES HAVING SACCHARIDE RESIDUE AT ONE END AND DIFFERENT FUNCTIONAL GROUP AT ANOTHER END

[75] Inventors: Kazunori Kataoka, Chiba; Yukio Nagasaki; Masao Kato, both of Ibaraki; Teruo Okano, Chiba; Teruo Nakamura, Shizuoka, all of Japan

[73] Assignee: Kazunori Kataoka, Chiba, Japan

[21] Appl. No.: 08/930,855

[22] PCT Filed: Apr. 12, 1996

[86] PCT No.: PCT/JP96/01020

§ 371 Date: Dec. 18, 1997

§ 102(e) Date: Dec. 18, 1997

[87] PCT Pub. No.: WO96/32434

PCT Pub. Date: Oct. 17, 1996

[30] Foreign Application Priority Data

Apr. 14, 1995 [JP] Japan .................................. 7-089373

[51] Int. Cl.⁶ ........................... C08G 65/08; C08G 65/32
[52] U.S. Cl. .......................... 525/54.2; 525/54.3; 536/4.1
[58] Field of Search .................... 525/54.2, 54.3; 536/4.1

[56] References Cited

U.S. PATENT DOCUMENTS

| 5,037,969 | 8/1991 | Minami et al. | 536/4.1 |
| 5,410,016 | 4/1995 | Hubbell et al. | 528/354 |

FOREIGN PATENT DOCUMENTS

| 0251304 | 7/1986 | European Pat. Off. . |
| 152393 | 7/1986 | Japan . |
| 279469 | 10/1993 | Japan . |
| 48450 | 2/1995 | Japan . |
| 300521 | 11/1995 | Japan . |
| 316285 | 12/1995 | Japan . |
| 92366 | 4/1996 | Japan . |

*Primary Examiner*—Nathan M. Nutter
*Attorney, Agent, or Firm*—Scully, Scott, Murphy & Presser

[57] ABSTRACT

This invention provides a heterotelechelic oligomer or polymer which is represented by the following formula:

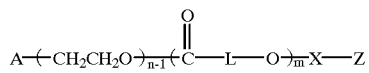

wherein A denotes a sugar residue, L denotes a linkage group represented by the following formula

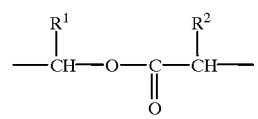

or

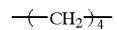

wherein $R^1$ and $R^2$ independently denote lower alkyl, aralkyl or aryl, X denotes a single bond or —$CH_2CH$—, Z denotes a group forming an unsaturated ester or ether, or a functional group such as halogen which binds to —$CH_2CH_2$—, n denotes an integer of 5–10,000, and m denotes an integer of 0 or 2–10,000.

This invention also provides a process to produce the above oligomer or polymer, and further a high molecular-micelle with use of a polyethylene oxide-polyester block polymer which has a sugar residue at its terminal. Said oligomer or polymer is expected to exhibit excellent bioavailability, and is also expected to be utilized in the field such as carriers for drug delivery or diagnostic reagents.

13 Claims, 7 Drawing Sheets

POLYETHYLENE OXIDES HAVING SACCHARIDE RESIDUE AT ONE END AND DIFFERENT FUNCTIONAL GROUP AT ANOTHER END

CONTINUING DATA

This application is filed under 35 USC 371 of JP96/01020, filed Apr. 12, 1996.

FIELD OF THE INVENTION

The present invention relates to an oligomer or polymer (heterotelechelic oligomer or polymer) which has a sugar on one end and a different functional group on the other end, and a method for the production of said oligomer or polymer.

Prior Arts

Polyethyleneoxide has properties such as solubility in water and non-immunogenicity, and its applications in biology and medical engineering are noted, such as its use as a modifier of biologically active substances such as proteins and drugs.

For example, it is known that when protein is modified with, polyethylene glycol, its immunogenicity is markedly reduced (Protein Hybrid, Yuji Inada, Hirotomo Maeda and Kyoritsu Shuppan (1988)). When the polyethylene oxide is bonded to protein in this way, a function group to react with the protein terminal must be on the end of the polyethylene oxide. Generally, various functional groups such as carboxyl group, amino group, hydroxyl group and mercapto group are present on the surface of a protein, and the selection of the functional group when reacting with the polyethylene oxide often has a great influence on the physiological activation of that protein.

Currently, most of the polyethylene oxide derivatives which are being engineered have a hydroxyl group on both ends, or a non reactive alkoxy group on one end and a hydroxyl group on the other end. Since the hydroxyl group has low reactivity compared to the aldehyde group and the amino group, there have been attempts to convert it to another functional group (Synth. Commun., 22(16), 2417–2424 (1992); J. Bioact. Compat. Polym., 5(2) 227–231 (1990). The manner of the reaction or use of polyethylene oxide has been disadvantageously limited when it is utilized as a modifier of protein in the above-mentioned way.

Furthermore, the importance of the hetero bonding to link a protein having a certain function with a compound having another function such as an antibody via polyethylene oxide has recently been noted. In this case, the polyethylene oxide derivative having a different functional groups on both ends is important. The method using a polyethylene oxide having a hydroxyl group at both ends as the raw material is used in order to synthesize this type of heteropolyethylene oxide (Poly(ethylene glycol) Chemistry; JM/Harris, Plenum Press, 1992). The product obtained by this type of method is, however, a mixture of unreacted matter, side reaction matter and over reaction matter modified on its both ends, and, therefore, this product needs to be refined by column operation or the like so that the desired product may be isolated, which process causes a large problem with yield and purity.

To overcome these types of problems, the inventors recently polymerized polyethylene oxide with an alkali metal salt of amino or alcohol having a function group as an initiator, and discovered a method to synthesize heteropolyethylene oxide quantitatively having different functional groups on both ends such as amino group, aldehyde group, mercapto group, carboxyl group and hydroxyl group (Japanese Patent Application No. 5-009168; Tokugan 5-194977; Tokugan 6-94532; Tokugan 6-117262; and Tokugan 6-228465).

However, quantitative synthesis of heteropolyethylene oxide having a sugar residue on one end has not yet been performed. Because of the characteristic interaction and affinity between the type of sugar and each component in the body, a compound having a characteristic affinity for biological components and having high bioavailability can be attained if a sugar group can be quantitatively introduced to one end of polyethylene oxide and a reactive functional group to the other end; such a compound would be a material which can be expected to be applied to carriers for drug delivery which have targeting properties and to precursors of diagnostic materials and the like.

The objective of this invention is therefore to produce a (heterotelechelic) polyethylene oxide derivative and a polyoxyethylene-polyester derivative having a sugar residue on one end and a reactive functional group other than sugar at the other end and to provide a method to produce such derivatives selectively and with ease and efficiency.

DISCLOSURE OF THE INVENTION

The inventors of this invention have found that, by meas of applying living polymerization to sugars whose hydroxyl groups are selectively protected and to ethylene oxide and lactone or lactide as cyclic monomers, there can be freely produced heterotelechelic oligomer and polymer which have a sugar on one end and a reactive functional group other than sugar on the other end and which have a narrow molecular weight distribution and which have a desired polymerization degree. Thus produced polyethylene oxide derivative is expected to show excellent bioavailability and to be conveniently used as a material or precursor in the field of biochemistry and/or medical treatment.

This invention provides a polyethylene oxide derivative which is represented by the following formula (I):

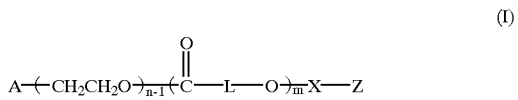

wherein A denotes a sugar residue represented by the following formula

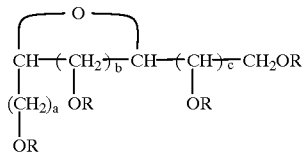

wherein the groups R independently denote the followings: one of the Rs denotes a linkage of covalent bond with the adjacent methylene group via oxygen atom; as for the other Rs, they sometimes denote hydrogen atom, $C_{1-5}$ alkyl, $C_{1-5}$ alkylcarbonyl or tri-$C_{1-5}$ alkylsilyl (these alkyls are similar or different), and, sometimes, two of said Rs in combination, while forming an acetal together with the oxygen atom to which the Rs are bound, denote $C_{3-5}$ alkylidene or benzylidene whose methine may be substituted with $C_{1-3}$ alkyl;

a denotes an integer of 0 or 1, b denotes an integer of 2 or 3, and c denotes an integer of 0 or 1, n denotes an integer of 5–10,000, L denotes a linkage group represented by the following formula

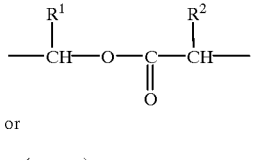

or

—(CH$_2$)$_4$— wherein $R^1$ and $R^2$ independently denote hydrogen atom, $C_{1-6}$ alkyl, aryl or $C_{1-3}$ alkylaryl, m denotes an integer of 0 or 2–10,000, X denotes a single bond or —CH$_2$CH$_2$—, and when X is a single bond, Z denotes hydrogen atom, alkali metal, acryloyl, methacryloyl, cinnamoyl, p-toluenesulfonyl, allyl, carboxymethyl, carboxyethyl, ethoxycarbonylmethyl, ethoxycarbonylethyl, 2-aminoethyl, 3-aminopropyl, 4-aminobutyl, vinylbenzyl, di-$C_{1-5}$ alkyloxy-$C_{2-3}$ alkyl or aldehyde-$C_{2-3}$ alkyl, while, when X is —CH$_2$CH$_2$— and m is 0, Z denotes hydroxyl, mercapto, amino or halogen atom.

In another aspect, this invention provides a process to produce a polyethylene oxide derivative represented by the above formula (I) which process comprises the following steps:

Step (1):

Ethylene oxide is polymerized in the presence of a polymerization initiator represented by the following formula (II)

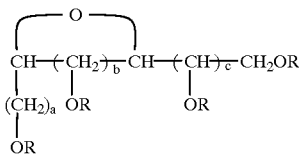

wherein the groups R independently denote the followings: one of the Rs denotes an alkali metal (M), e.x., sodium, potassium or cesium; as for the other Rs, they sometimes denote $C_{1-5}$ alkyl, $C_{1-5}$ alkylcarbonyl or tri-$C_{1-5}$ alkylsilyl (these alkyls are similar or different), and, sometimes, two of said Rs in combination, while forming an acetal together with the oxygen atom to which the Rs are bound, denote $C_{3-5}$ alkylidene or benzylidene whose methine may be substituted with $C_{1-3}$ alkyl; a denotes an integer of 0 or 1, b denotes an integer of 2 or 3, and c denotes an integer of 0 or 1.

Step (2):

If need be, the oligomer or polymer obtained in the above Step (1) represented by the following formula (III)

(III)

wherein A and n are as defined in formula (I) is either (i) hydrolyzed or (ii) made to react with

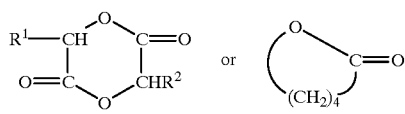

wherein $R^1$ and $R^2$ are as defined in formula (I) so that there may be obtained oligomer or polymer represented by the following formula (IV)

(IV)

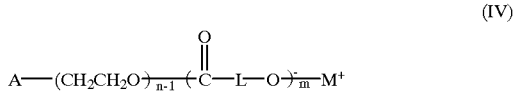

wherein A, L, m and n are as defined in formula (I).

Step (3):

If necessary, the oligomer or polymer obtained in Step (1) or Step (2) is made to react either with (i) acrylic acid, methacrylic acid, p-toluene-sulfonic acid or reactive derivative thereof or with (ii) the halide represented by the following formula (V)

halo-E         (V)

wherein halo denotes chlorine, bromine or iodine, E denotes allyl, carboxymethyl, ethoxycarbonylmethyl, ethoxycarbonylethyl, vinylbenzyl, N-phthalimide ethyl, N-phthalimide propyl or N-phthalimide butyl.

Step (4):

If necessary, groups R of the sugar residue A are eliminated except the above-mentioned likage.

In the above-stated manner, this invention provides a novel heterotelechelic polyethylene oxide or polyyethylene oxide-polyester derivative represented by formula (I) which is mono-dispersible or mono-modal polymer or oligomer having any polymerization degree depending on objective, and the invention also provides method to efficiently produce said polymer or oligomer.

The derivative represented by formula (I) can be used as a carrier for the support or drug delivery of various kind of medicines. When suitable protein, for example, antibodies and the like, are bound via functional group of the derivative, said derivative is expected to be usable as a carrier having targeting properties for a medicine or as a diagnostic reagent. In particular, the derivative wherein m in formula (I) denotes an integer of 2–10,000, has usability as a carrier for supporting medicines since such a derivative forms a stable high molecular micelle in an aqueous solvent.

DETAILED DESCRIPTION OF THE INVENTION

Figure 1:
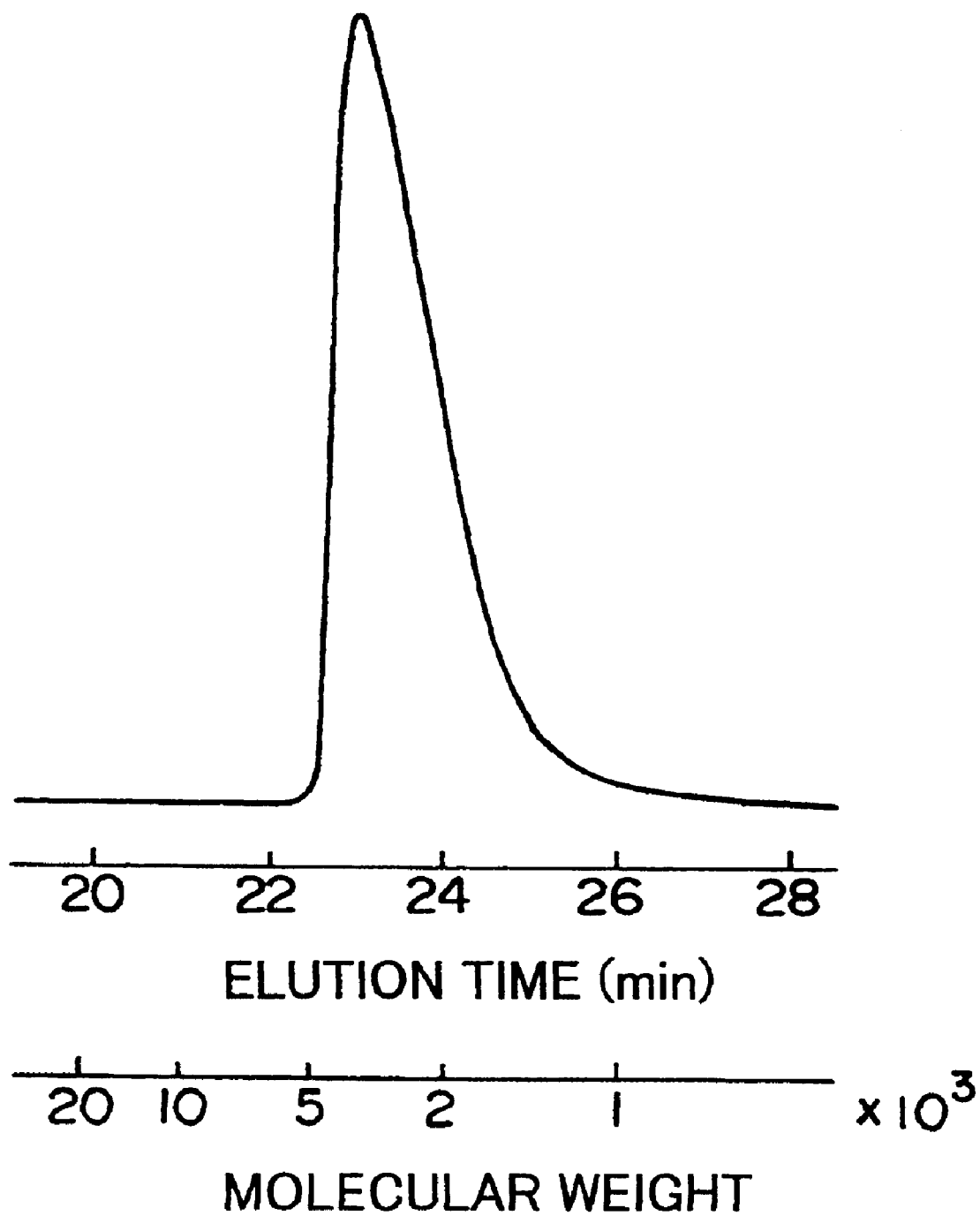
FIG. 1 shows a gel permeation chromatogram of the heterotelechelic polyethyleneoxide (i.e., the sample of Example 1 mentioned later) which quantitatively has a 1,2;5,6-di-O-isopropylidene-D-glucofuranose residue at the α-terminal and a hydroxy group at ω-terminal (Condition: Column: TSK-Gel (G4000 H×L, G3000 H×L, G2500 H×L); Eluent: THF (containing 2% triethylamine); Flow rate: 1 ml/min.)

The group A in the polyethylene oxide derivative of formula (I) of this invention may be either made from a natural product or a derivative of a natural product or a chemical synthetic so long as it is a residue of monosaccharide represented by the formula

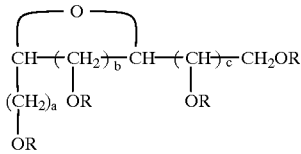

wherein R, a, b and c are as defined above.

Examples of sugars from natural products from which such a sugar residue can be conveniently derived include, not restrictively, the followings: glucose, galactose, mannose, fructose, ribose, arabinose, xylose, lyxose, allose, altrose, gulose, idose and talose. What is most preferable among these varies dependent on the object of use of the polyethylene oxide derivative of this invention, and, therefore, cannot be limited. From the viewpoint of availability of raw material, however, glucose, galactose, mannose, fructose, ribose and xylose are generally preferable. From such a viewpoint, glucose and galactose are especially preferable.

The groups R in the above sugar residue, which are intended to protect all the hydroxyl groups of the sugar residue, subjecting the derivative of formula (I) to further reactions, are either such groups as are capable of selective deprotection when necessary or hydrogen atoms, except the single R which is a linkage of covalent bond of said sugar residue with the α-terminal methylene group of the polyethylene oxide segment of the derivative of formula (I) via oxygen atom to which said R is bound. Concrete examples of such protecting group include $C_{1-5}$ alkyl, $C_{1-5}$ alkylcarbonyl and tri-$C_{1-5}$ alkylsilyl groups. The alkyl portion of these groups may be straight chain or branched chain alkyl, for example, methyl, ethyl, propyl, iso-propyl, butyl, sec-butyl, tert-butyl, pentyl and iso-pentyl. As for tri-$C_{1-5}$ alkylsilyl, three alkyl portions therein may be similar or different. Preferable examples of this group include trimethylsilyl, triethylsilyl and tripropylsilyl wherein the alkyl portions therein are similar to one another.

In another case, two of said Rs in combination, while forming an acetal

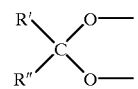

together with the oxygen atom to which the Rs are bound, denote $C_{3-5}$ alkylidene such as isopropylidene, 1-butylidene, 2-butylidene or 3-pentylidene, and benzylidene whose methine may be substituted with $C_{1-3}$ alkyl such as benzylidene

and methylbenzylidene

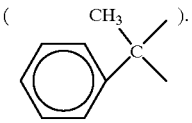

When two Rs form these acetals, these groups R can be selectively eliminated with ease, and there can be conveniently produced a sugar residue wherein R denotes hydrogen atom (hydroxyl group is deprotected).

The marks a, b and c in the above formula denote integers which vary according to the kind of sugar selected as a starting material. The mark a is 0 or 1, b is 2 or 3, and c is 0 or 1. When glucose is used as a starting material, for example, a is 0, b is 3 and c is 0 in the case of D-glucopyranose in the form of intramolecular hemiacetal, while, in the case of D-glucofuranose, a is 0, b is 2 and c is 1. Both of these forms are therefore included in the above sugar residue.

When galactose is used as a starting material, on the other hand, a is 0, b is 3 and c is 0.

The mark n in the segment $-\!(CH_2CH_2O)_{n-1}$ derived from ethylene oxide in formula (I) can theoretically be any number when the proportion of the amount of ethylene oxide (monomer) to polymerization initiator is adjusted in the production method of this invention by means of living polymerization. In order to achieve the object of this invention, n is preferably be an integer of 5–10,000.

When n is less than 5, it is generally difficult to keep narrow the molecular weight distribution of oligomer (or polymer) having such a number n, and, thus, it may be hard to produce mono-dispersible or mono-modal oligomer (or polymer).

On the other hand, n is an integer of at most 10,000. As stated above, the production method of this invention can theoretically provide a polymer of higher polymerization degree. When the polyethylene oxide derivative of this invention is to be used as a precursor for a carrier to support medicines or the like, however, n is preferably be not higher than 10,000.

Incidentally, it should be understood that the inventors contemplate using the derivative of this invention as an intermediate from which to extend further oxyethylene or ester segments. More concretely, however, n in the derivative of formula (I) of this invention is preferably an integer of 10–200, more preferably, 20–50.

The mark L in the segment (also called polyester segment) derived from lactide or lactone of formula (I)

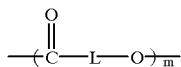

denotes

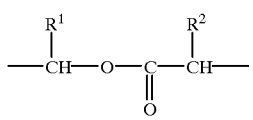

or —(CH$_2$)$_4$—.

The above $R^1$ and $R^2$ independently denote hydrogen atom, $C_{1-6}$ alkyl, aryl or $C_{1-3}$ alkylaryl.

Examples of $C_{1-6}$ alkyl include straight chain or branched chain lower alkyl group such as methyl, ethyl, propyl, iso-propyl, butyl, sec-butyl, tert-butyl, pentyl, iso-pentyl and hexyl. Preferable example of aryl is phenyl, and examples of $C_{1-3}$ alkylaryl include benzyl, ethylbenzene and the like.

These segments are usually derived from lactide of α-hydroxycarboxylic acid. In consideration of bioavailability, they are preferably derived from glycolic acid, lactic acid, 2-hydroxyisobutyric acid or such a lactide as comprises two of these in combination. In other words, it is preferable that $R^1$ and $R^2$ independently denote hydrogen atom, methyl or isopropyl group.

The segment

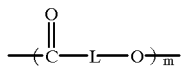

is optional. The mark m may denote 0 (said segment is absent) or an integer of 2–10,000, and may form a block polymer. When a block polymer is formed, this segment generally provides the polyethylene oxide derivative of this invention with a hydrophobic portion. The preferable size of m is therefore dependent on the object of use of the derivative (block polymer) of this invention or on the properties of the groups $R^1$ and $R^2$. Generally, however, m is preferably 5–200, more preferably, 10–100.

The mark X in —X—Z in formula (I) is either a single bond in the case where Z is directly covalently bound to the oxygen atom at ω-position of the following segments

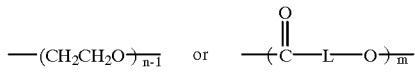

or ethylene (—CH$_2$CH$_2$—). Therefore, when m is 0, this ethylene group can be derived from —CH$_2$CH$_2$—OH which is formed on account of the addition of ethylene oxide.

When X is a single bond, Z can be hydrogen atom or alkali metal. In this case, the compound of this invention is provided as a reaction product or its hydrolyzate from a living polymerization wherein there are used the anion of the sugar residue A as a polymerization initiator, ethylene oxide as a monomer, and, according to circumstances, lactide or lactone. Typical examples of alkaline metal therefore include sodium, potassium and besium.

When Z is other than alkali metal and hydrogen atom, the polyethylene oxide derivative of this invention provides various kind of ether and ester having a different functional group which is formed via the ω-terminal hydroxyl group. Z can therefore be a group which is capable of forming ester such as acryloyl (—COCH=CH$_2$), methacryloyl (—COC(CH$_3$)=CH$_2$), cinnamoyl

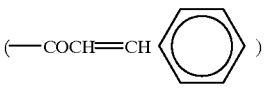

and p-toluenesulfonyl

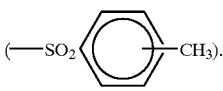

On the other hand, examples of such Z as can form an ether include allyl (—CH$_2$—CH=CH$_2$), carboxymethyl (—CH$_2$COOH), carboxyethyl (—CH$_2$CH$_2$COOH), ethoxycarbonylmethyl (—CH$_2$COOC$_2$H$_5$), ethoxycarbonylethyl (—CH$_2$CH$_2$COOC$_2$H$_5$), 2-aminoethyl (—CH$_2$CH$_2$NH$_2$), 3-aminopropyl (—CH$_2$CH$_2$CH$_2$NH$_2$), 4-aminobutyl (—CH$_2$(CH$_2$)$_2$CH$_2$NH$_2$) and vinylbenzyl

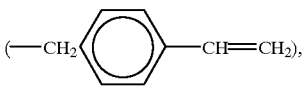

and di-$C_{1-5}$alkyloxy-$C_{2-3}$-alkyl such as 2,2-dimethyloxyethyl (—CH$_2$CH(OCH$_3$)$_2$), 2,2-diethoxyethyl (—CH$_2$CH(OC$_2$H$_5$)$_2$) and 3,3-dimethoxypropyl (—CH$_2$CH$_2$CH(OCH$_3$)$_2$), and aldehyde-$C_{2-3}$ alkyl (—(CH$_2$)$_{1-2}$CHO).

Furthermore, when X denotes —CH$_2$CH$_2$— and m denotes 0 (zero), Z can be hydroxyl, mercapto (—SH), amino (—NH$_2$) and halogen such as chlorine, bromine and iodine. The derivative of formula (I) having these substituents can be obtained from ω-terminal p-toluene sulfonated compound through a known reaction.

The following Table 1 shows concrete examples of polyethylene oxide derivatives (compounds) of this invention which are composed of the above-mentioned substituents.

TABLE 1

$$A\text{---}(CH_2CH_2O)_{n-1}\text{---}\underset{O}{\overset{\|}{C}}\text{---}L\text{---}O)_m X\text{---}Z$$

$$\text{---}(\underset{O}{\overset{\|}{C}}\text{---}L\text{---}O)\text{---}$$

| Compound No. | A | Site of sugar linkage | n-1 | (C-L-O) | m | X | Z |
|---|---|---|---|---|---|---|---|
| 1 | Glu(p)*[1] | 3–0 | 20~50 | — | 0 | — | H |
| 2 | Glu(p) | 3–0 | 20~50 | — | 0 | — | K |
| 3 | Glu(p) | 3–0 | 20~50 | — | 0 | — | COC(CH$_3$)=CH$_2$ |
| 4 | Glu(p) | 3–0 | 20~50 | — | 0 | — | COCH=CH$_2$ |
| 5 | Glu(p) | 3–0 | 20~50 | — | 0 | — | SO$_2$—C$_6$H$_4$—CH$_3$ |
| 6 | Glu(p) | 3–0 | 20~50 | — | 0 | — | CH$_2$—CH=CH$_2$ |
| 7 | Glu(p) | 3–0 | 20~50 | — | 0 | — | CH$_2$COOC$_2$H$_5$ |
| 8 | Glu(p) | 3–0 | 20~50 | — | 0 | — | CH$_2$CH$_2$COOC$_2$H$_5$ |
| 9 | Glu(p) | 3–0 | 20~50 | — | 0 | — | CH$_2$CH$_2$NH$_2$ |
| 10 | Glu(p) | 3–0 | 20~50 | — | 0 | — | CH$_2$—C$_6$H$_4$—CH=CH$_2$ |
| 11 | Glu(p) | 3–0 | 20~50 | — | 0 | — | CH$_2$CHO |
| 12 | Glu(p) | 3–0 | 20~50 | — | 0 | — | CH$_2$CH$_2$CHO |
| 13 | Glu(p) | 3–0 | 20~50 | — | 0 | —CH$_2$CH$_2$— | Cl |
| 14 | Glu(p) | 3–0 | 20~50 | — | 0 | —CH$_2$CH$_2$— | SH |
| 15~22 | Deprotected*[2] compounds corresponding to Compound Nos. 1, 3, 4, 6, 9, 10, 13 and 14 | | | | | | |
| 23 | Glu (deprotected) | 3–0 | 20~50 | — | 0 | — | CH$_2$COOH |
| 24 | Glu (deprotected) | 3–0 | 20~50 | — | 0 | — | CH$_2$CH$_2$COOH |
| 25 | Glu (deprotected) | 3–0 | 20~50 | — | 0 | — | CH$_2$CHO |
| 26 | Glu (deprotected) | 3–0 | 20~50 | — | 0 | — | CH$_2$CH$_2$CHO |
| 27~52 | Compounds corresponding to Compound Nos. 1~26, wherein site of sugar linkage is 6–0 | | | | | | |
| 53~66 | Compounds corresponding to Compound Nos. 1~14, wherein Glu(p) is Gal(p) and the site of sugar linkage is 6–0 | | | | | | |
| 67~74 | Compounds corresponding to Compound Nos. 1, 3, 4, 6, 9, 10, 13 and 14, wherein Glu(p) is Gal(deprotected) and the site of sugar linkage is 6–0 | | | | | | |
| 75~78 | Compounds corresponding to Compound Nos. 23~26, wherein Glu(deprotected) is Gal(deprotected) and the site of sugar linkage is 6–0 | | | | | | |
| 79~92 | Compounds corresponding to Compound Nos. 1~14, wherein Glu(P) and Man(P)*[4] and the site of sugar linkage is 4–0 | | | | | | |
| 93~100 | Compounds corresponding to Compound Nos. 1, 3, 4, 6, 9, 10, 13, and 14, wherein Glu(p) is Man(deprotected) and the site of sugar linkage is 4–0 | | | | | | |
| 101~104 | Compounds corresponding to Compound Nos. 23~26, wherein Glu(deprotected) is Man(deprotected) and the site of sugar linkage is 4–0 | | | | | | |
| 105 | Glu(p) | 3–0 | 20~50 | —C(=O)—CH(CH$_3$)—O—C(=O)—CH(CH$_3$)—O— | 20~100 | — | H |
| 106 | Glu(p) | 3–0 | 20~50 | —C(=O)—CH(CH$_3$)—O—C(=O)—CH(CH$_3$)—O— | 20~100 | — | K |
| 107 | Glu(p) | 3–0 | 20~50 | —C(=O)CH$_2$CH$_2$CH$_2$CH$_2$O— | 20~100 | — | H |

TABLE 1-continued $$A\text{---}(CH_2CH_2O)_{\overline{n\text{-}1}}(\overset{O}{\overset{\|}{C}}\text{---}L\text{---}O)_{\overline{m}}X\text{---}Z$$

| Compound No. | A | Site of sugar linkage | n-1 | $(\overset{O}{\overset{\|}{-C}}\text{---}L\text{---}O-)$ | m | X | Z |
|---|---|---|---|---|---|---|---|
| 108 | Glu(p) | 3–0 | 20~50 | $-\overset{O}{\overset{\|}{C}}CH_2CH_2CH_2CH_2O-$ | 20~100 | — | K |
| 109~118 | Gal(p) | 6–0 | 20~50 | $-\overset{O}{\overset{\|}{C}}-\underset{CH_3}{\overset{\|}{CH}}-O-\overset{O}{\overset{\|}{C}}-\underset{CH_3}{\overset{\|}{CH}}-O-$ | 20~100 | — | Groups corresponding to Compound Nos. 3~12 |

119~128 Compounds corresponding to Gal (deprotected) of Compound Nos. 109~118
129~132 Compounds corresponding to Compound Nos. 105~108, wherein site of sugar linkage is 6–0

NOTE
*¹⁾Glu(P) means that the hydroxyl groups other than those at the 3-position of glucose are protected with isopropylidene group.
*²⁾"deprotected" means that isopropylidene group or benzylidene group is eliminated to form a hydroxy group.
*³⁾Gal(P) means that the hydroxyl groups other than those at the 6-position of galactose are protected with 1,2-di-isopropylidene group.
*⁴⁾Man(P) means that the hydroxyl groups other than those at the 4-position of mannose are protected with isopropylidene group.

The polyethylene oxide derivatives provided by the present invention can be produced efficiently by the process of this invention which comprises the following steps:

Step (1):
Alkali metal (e.x., sodium, potassium or cesium) glycoside of formula (II)

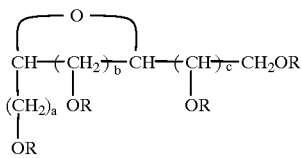

wherein R, a, b and c are as defined above
is subjected to living polymerization with ethylene oxide as a reaction initiator.

The alkali metal glycoside of formula (II) can be produced by protecting hydroxyl groups of a monosaccharide except one hydroxyl group and then metallizing the monosaccharide. This metallization can be achieved by using, as a metallizer, alkali metal such as sodium and potassium, organic metal such as sodium naphthalene, potassium naphthalene, cumyl potassium, cumyl cesium, and metal hydroxide such as sodium hydroxide and potassium hydroxide.

Thus obtained compound of formula (II) can preferably be made to react with ethylene oxide either in the absence of solvent or in an anhydrous aprotic solvent within a wide range of temperature of −50° C. to 300° C., preferably 10° C. to 60° C., conveniently at a room temperature (20° C. to 30° C.). The reaction may be conducted either under pressure or under reduced pressure. Usable solvents, although not restricted, include benzene, toluene, xylene, tetrahydrofuran and acetonitrile. Usable reactors, although not restricted in particular, include round-bottomed flask, autoclave and pressure resistant sealed tube. The reactor is preferably airtight, and is more preferably filled with inert gas. Reaction solution has a concentration of 0.1 to 95% by weight, preferably 1 to 80% by weight, most preferably 3 to 10% by weight.

Thus obtained polymer of formula (III) is itself included in the derivatives of formula (I) of the present invention. Furthermore, when the polymer is hydrolyzed or when the protecting group of hydroxyl is eliminated from sugar residue, there can be provided a derivative of the present invention wherein m denotes 0 and —X—Z denotes hydrogen atom in formula (I).

Step (2):
An oligomer or polymer represented by formula (III)

(III)

wherein A and n are as defined above, and M denotes sodium, potassium or cesium
is allowed to react with a cyclic monomer represented by the following formula:

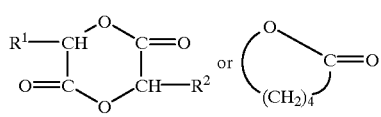

wherein R¹ and R² are as defined above.

Although reaction temperature is not restricted, this step can be performed at a room temperature as in Step (1). Moreover, this step can be achieved by adding a cyclic monomer to the reaction mixture of Step (1).

The amount of monomer used in Steps (1) and (2) can be adjusted according to the polymerization degree which is shown by the number denoted by n and m in the desired formula (I). In Step (1), for example, the proportion of the compound of formula (II) to ethylene oxide used is, in molar ratio, 1:1 to 1:10,000, preferably 1:5 to 1:10,000, most preferably 1:20–200 to 1:50–200.

Step (3):

The block oligomer or polymer of formula (IV) obtained in Step (2) is itself included in the derivatives of formula (I) of the present invention. Furthermore, when said oligomer or polymer is hydrolyzed or, under circumstances, when protecting groups of hydrogyl groups in the sugar residue are eliminated, there can be provided the derivatives of the present invention wherein m in formula (I) denotes an integer of 2–10,000 and —X—Z denote a hydrogen atom.

In Step (3), the alkali metal alkoxide of the above formula (III) or (IV) is hydrolyzed to become an ω-terminal hydroxyl body, which is (i) made to react with acrylic acid, methacrylic acid or p-toluene sulfonic acid in an inert organic solvent to form an ω-terminal esterified compound, or (ii) allowed to react with a halide of formula (V)

halo-E     (V)

wherein halo and E are as defined above to form an ω-terminal etherified compound.

These reactions can be carried out by known esterification or etherification process. Concrete processes are shown in Examples mentioned later. As for the organic acid in the above (i), there are conveniently employed reactive derivative of acid anhydride or acid halide.

In the case of introducing a mercapto group to the ω-terminal for example, after the tosylation of the ω-terminal of hydrolyzate of formula (III) or (IV) with p-toluenesulfonylchloride, thioester group is introduced to the ω-terminal by the reaction with an electrophilic agent such as sodium thioacetate, potassium thioacetate, or potassium hydrosulfide; then hydrolysis of the ω-terminal thioester is performed at the same time as de-protection of the sugar residue by processing with an alkali or acid, and the compound shown in formula (I) is attained. Also, another method to attain the compound shown in formula (I) is the coupling reaction of the hydrolyzate of formula (III) or (IV) with a p-toluenesulfonic acid ester having an S—S bond such as dithiodiethanol ditosylate, then a reducing reaction to attain a mercapto terminal group, followed by deprotection of the sugar residue by processing with an acid or alkali.

In the case of introducing an amino group to the ω-terminal for example, the hydrolyzate of formula (III) or (IV) is reacted with an electrophilic agent, N-(2-bromoethyl)phthalimide, N-(3-bromopropyl)phthalimide, 1-bromo-2-(benzeneamide)ethane, N-(2-bromoethyl)benzyl carbamate; then hydrolysis of the ω-terminal imide bond is performed at the same time as de-protection of the sugar group by processing with an alkali or acid, and the compound shown in formula (I) is attained.

In the case of introducing an aldehyde group to the ω-terminal for example, a halogenated alkyl having an acetal group such as 2,2-dimethoxyethylchloride, 2,2-diethoxyethylchloride, 2,2-dimethoxyethylbromide, 2,2-diethoxyethylbromide, or 3,3-dimethoxypropylchloride is reacted; then hydrolysis of the ω-terminal acetal is performed at the same time as de-protection of the sugar residue by processing with an alkali or acid, and the compound shown in formula (I) is attained.

Step (4):

When the protecting groups of the sugar residue are eliminated if necessary, the oligomer or polymer obtained in the above provides the derivatives of formula (I) of the present invention wherein the protecting groups R (other than linkage) of the sugar residue are eliminated (resultantly, R denotes hydrogen atom). Two of the protecting groups R preferably form an acetal together, so that the protecting groups R are selectively eliminated. As for the eliminating reaction, acid hydrolysis with use of trifluoroacetic acid is convenient.

The reagent used during hydrolysis of R of the sugar residue and protecting groups (when the group Z has protecting groups) of the other portions may be an acid such as hydrochloric acid, sulfuric acid, nitric acid, formic acid and hydrogen fluoride, as well as the above trifluoroacetic acid or alkali such as sodium hydroxide and potassium hydroxide. Also, reducing agent such as lithium aluminum hydride can be used.

In the method for hydrolysis, the polymer attained as above is dissolved in 0.01N–10N, preferably 0.1N–5N acid or alkali. The reaction temperature is 0–100° C., preferably 10–80° C., and most preferably 20–40° C.; the reaction time is 1 minute to 200 hours, preferably 30 minutes to 100 hours, and most preferably 1–2 hours.

With hydrolysis in this manner, the polyethylene oxide derivative shown in formula (I) and quantitatively having a sugar group on one end and a functional group other than sugar on the other end can be selectively attained.

After the end of the reaction, polyethylene oxide derivative which is the objective can be isolated as a precipitate by putting the reaction solution in a solution in which the polyethylene oxide is not soluble such as diethylether, isopropyl alcohol, or hexane. Also, it can be isolated and refined using methods such as dialysis, ultrafiltration, adsorbent processing, and the method with column chromatograms.

In this manner, the present invention provides monomodal derivatives represented by formula (I) which have narrow molecular weight distribution and desired molecular weight. These derivatives are novel heterotelechelic oligomers or polymers which are expected to have excellent bioavailability.

The following is concrete examples of the present invention. These examples are, however, not intended to restrict this invention.

Typical reaction scheme:

For easy understanding of this invention, the following schemes show the reaction system for the synthesis of the hetero bivalent poly(ethyleneglycol) having a reduced carbohydrate group on one end, this being a mode of this invention.

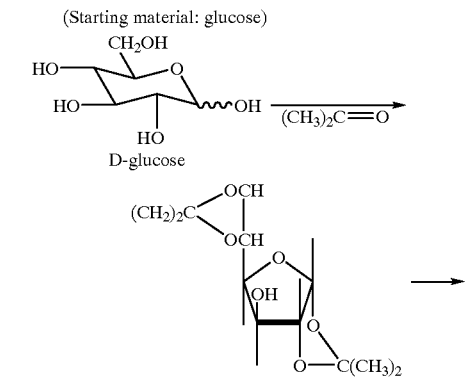

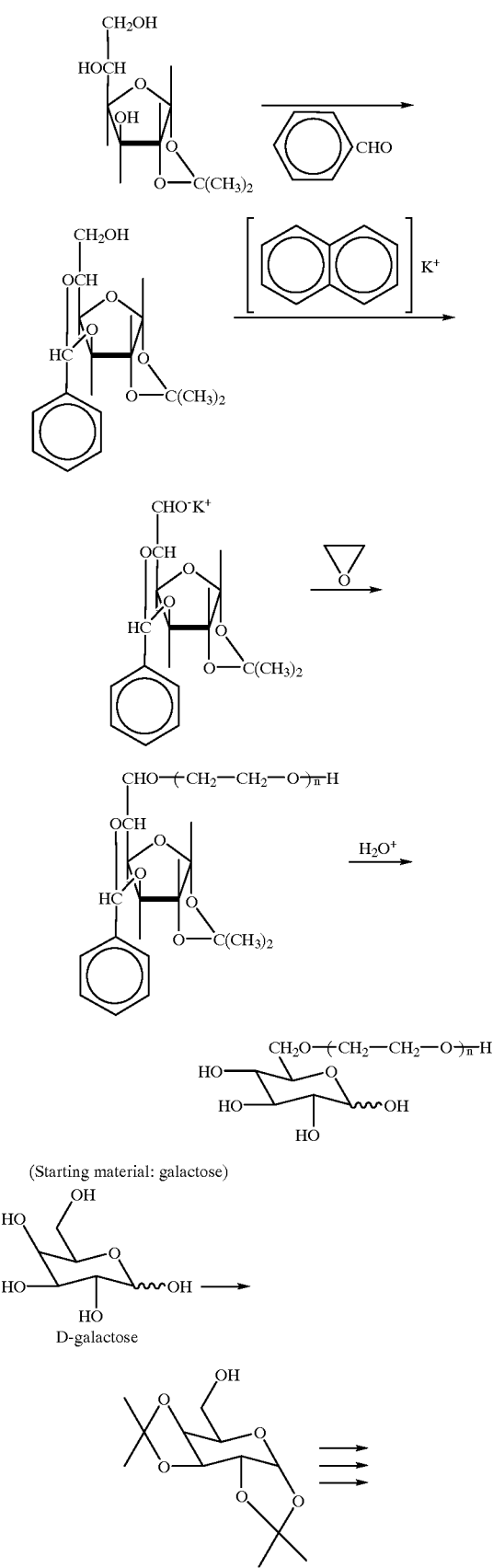

(Starting material: galactose)

D-galactose

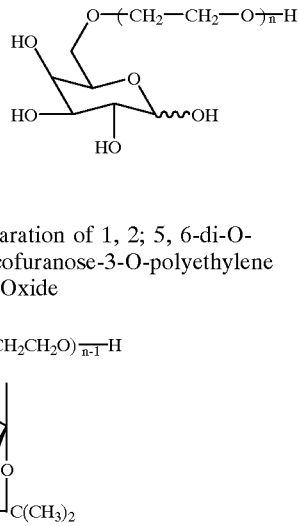

EXAMPLE 1: Preparation of 1, 2; 5, 6-di-O-isopropylidene-D-glucofuranose-3-O-polyethylene Oxide

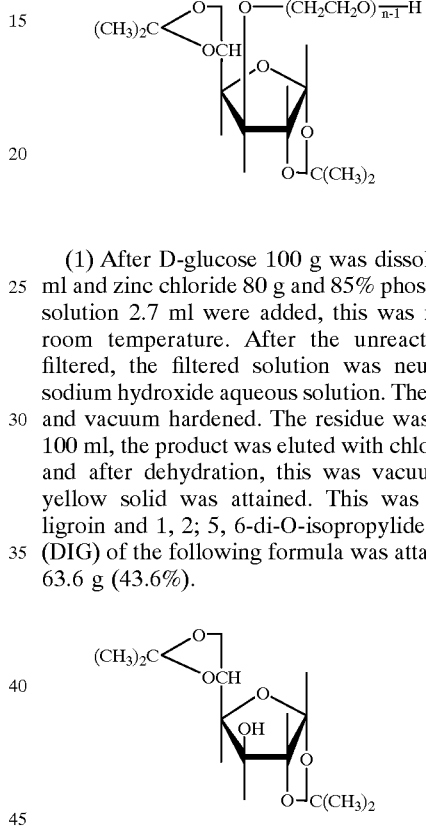

(1) After D-glucose 100 g was dissolved in acetone 660 ml and zinc chloride 80 g and 85% phosphoric acid aqueous solution 2.7 ml were added, this was reacted 32 hours at room temperature. After the unreacted D-glucose was filtered, the filtered solution was neutralized with 2.5N sodium hydroxide aqueous solution. The salt was filtered out and vacuum hardened. The residue was dissolved in water 100 ml, the product was eluted with chloroform (100 ml×3), and after dehydration, this was vacuum hardened and a yellow solid was attained. This was recrystallized with ligroin and 1, 2; 5, 6-di-O-isopropylidene-D-glucofuranose (DIG) of the following formula was attained. The yield was 63.6 g (43.6%).

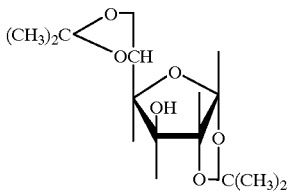

(2) DIG 260 mg. THF 20 ml, and potassium naphthalene 0.5 mol/L-tetrahydrofuran solution 2 ml were added to the reaction container, agitated for 3 minutes in an argon atmosphere, and 3-O-potassium-1, 2; 5, 6-di-O-isopropylidene-D-glucofuranose was produced. Ethylene oxide 5.7 g was added to this solution and agitated at room temperature under 1 atm. After reacting for two days, a small amount of water was added and the reaction as stopped; then the reaction solution was poured into ether and the polymer produced was precipitated. The precipitate attained was refined by freeze drying from benzene. The yield was 5.6 g (94%). The polymer attained through gel permeation chromatography was monomodal, the molecular weight of the polymer was 2500 (FIG. 1).

According to the proton nuclear magnetic resonance spectra in the chloroform deuteride of the polymer attained, this polymer was confirmed to be heterotelechelic oligomer quantitatively having 1 2; 5, 6-di-O-isopropylidene-D-glucofuranose group on the α-terminal and hydroxyl group on the ω-terminal and having the polyethylene oxide (PEO)

Figure 2:
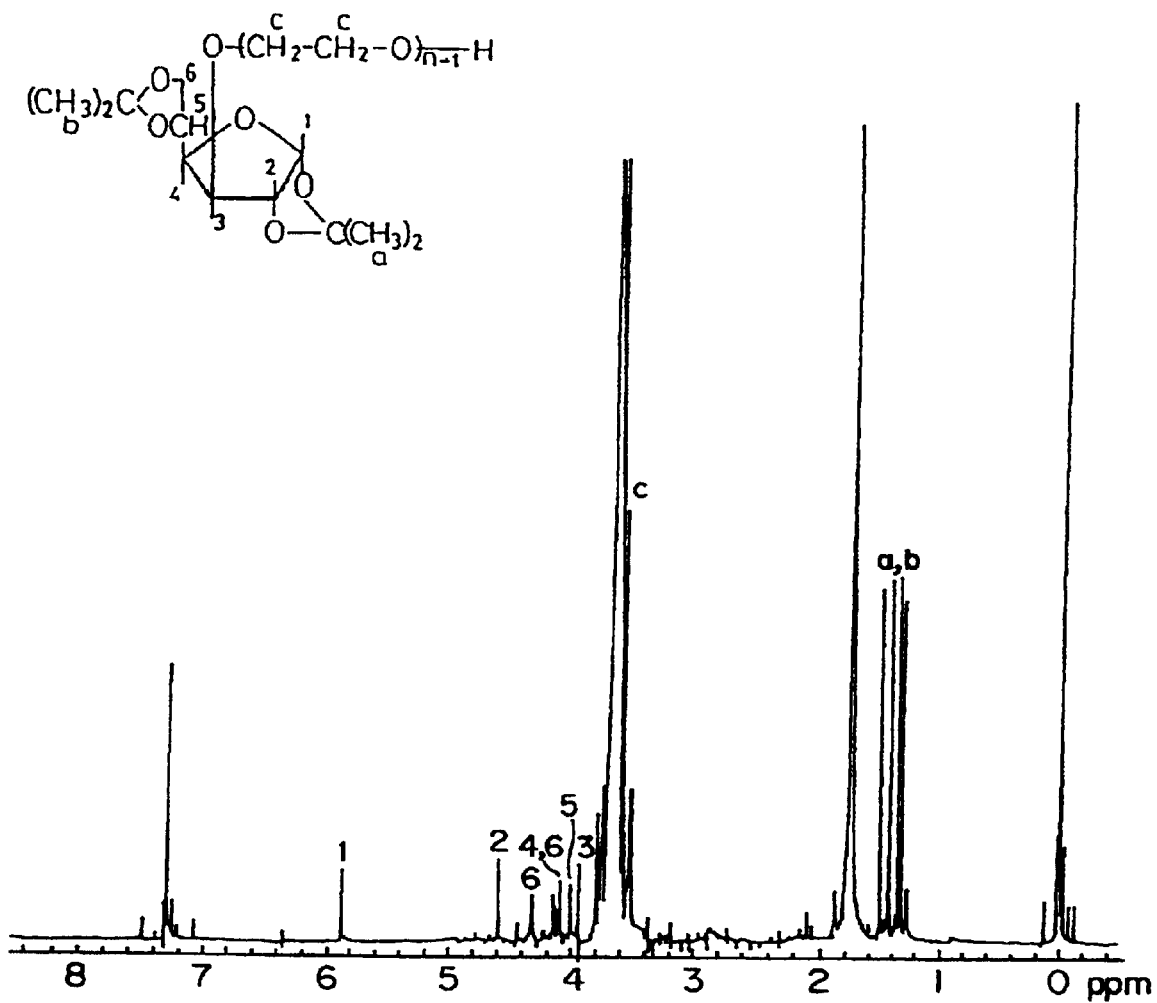
FIG. 2 shows proton nuclear magnetic resonance spectra of the heterotelechelic polyethyleneoxide (i.e., the sample of Example 1 mentioned later) which quantitatively has a 1,2;5,6-di-O-isopropylidene-D-glucofuranose residue at α-terminal and a hydroxy group at ω-terminal.
Figure 3:
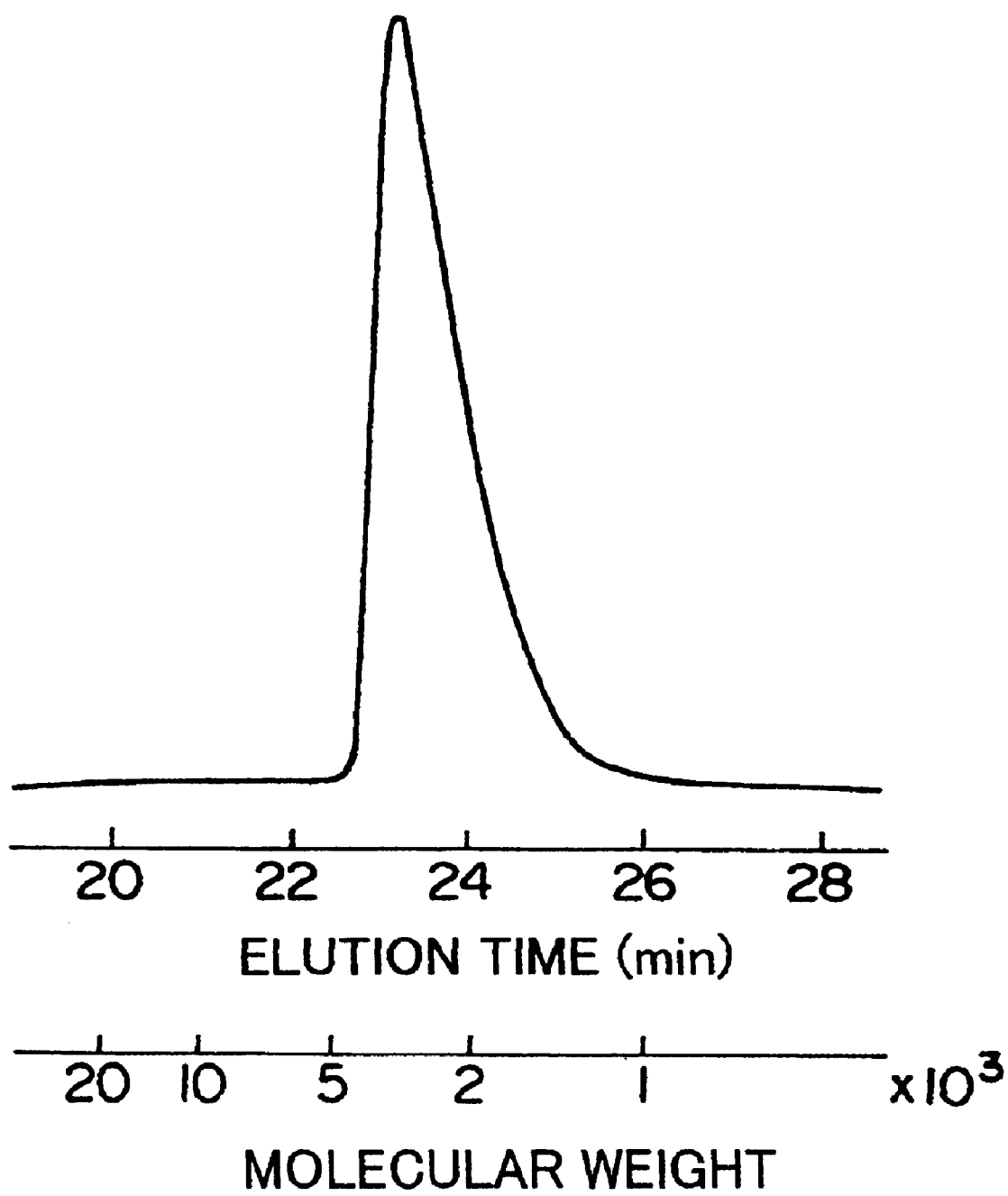
FIG. 3 shows a gel permeation chromatogram of the heterotelechelic polyethyleneoxide (the sample of Example 2 mentioned later) which quantitatively has a 3,5-O-benzylidene-1,2-O-isopropylidene-D-glucofuranose residue at α-terminal and a hydroxy group at ω-terminal (operational condition is the same as in FIG. 1).

(FIG. 2). The number average molecular weight of the polymer determined by the integral ratio of the spectra was 2400.

EXAMPLE 2: Preparation of 3, 5-O-benzylidene-1, 2-O-isopropylidene-D-glucofuranose-6-O-polyethylene Oxide

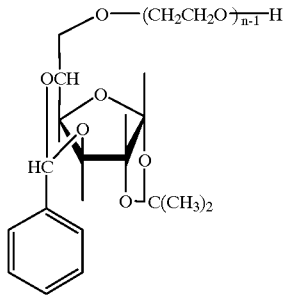

(1) DIG 10 g was dissolved in methanol 40 ml, 0.8% sulfuric acid aqueous solution 50 ml was added, and this was left standing at room temperature for 23 hours; then barium carbonate was added and this was neutralized, after boiling for 10 minutes, the salt was filtered out. Benzaldehyde 18 ml and zinc chloride 6.0 g were added to the white solid attained (7.5 g) after solvent distillation and this was agitated fiercely for 6 hours at room temperature. The sample attained was recrystallized from benzene and the 3, 5-O-benzylidene-D-glucofuranose (BIG) of the following formula was attained. The yield was 1.8 g (17.5%).

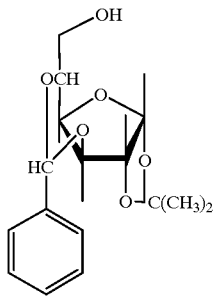

Figure 5:
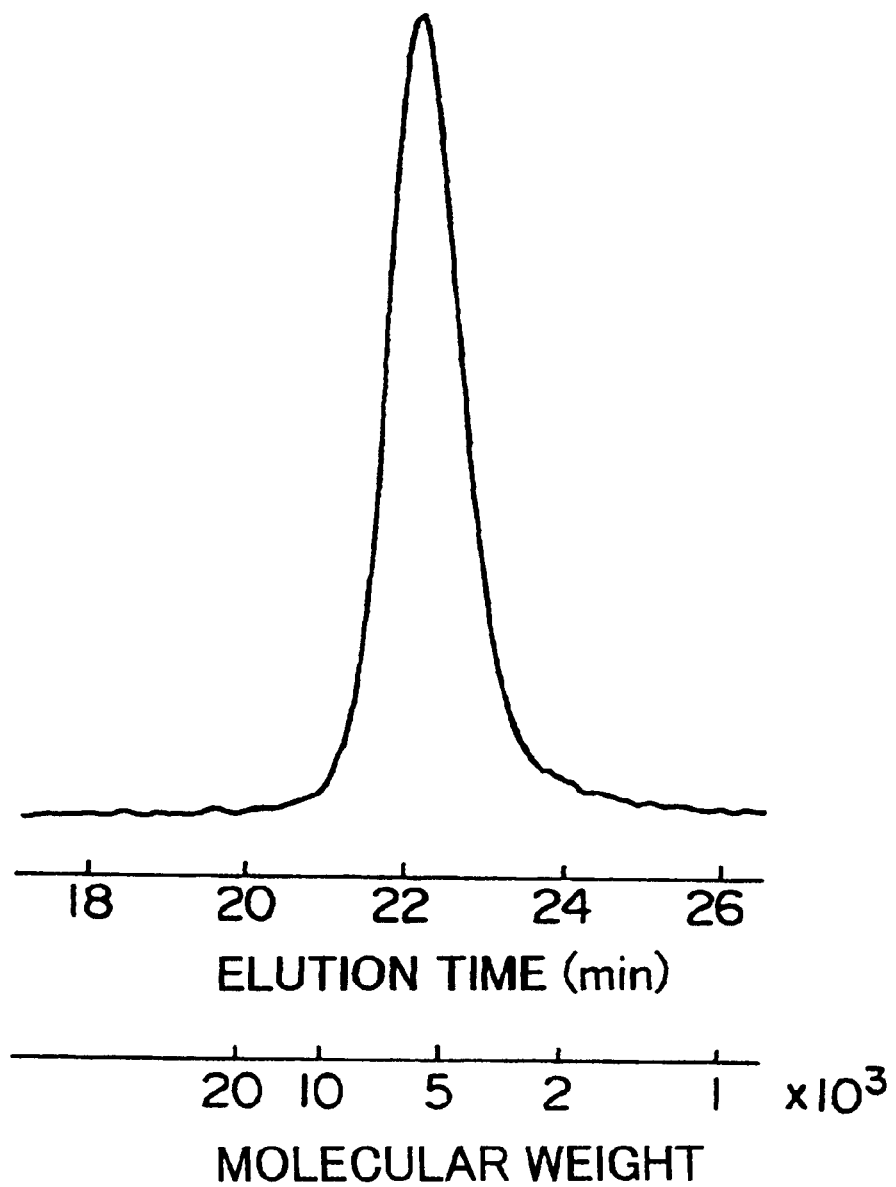
FIG. 5 shows a gel permeation chromatogram of the heterotelechelic polyethyleneoxide (the sample of Example 3 mentioned later) which quantitatively has a 1,2;3,4-di-O-isopropylidene-D-galactopyranose residue at α-terminal and a hydroxy group at ω-terminal (operational condition is the same as in FIG. 1 except that THF was used as an eluent).

(2) BIG 308 mg, THF 20 ml, and potassium naphthalene 0.5 mol/L tetrahydrofuran solution 2 ml were added to the reaction container and agitated for 3 minutes in an argon atmosphere; 6-O-potassium-3, 5-O-benzylidene-1, 2-O-isopropylidene-D-glucofuranose was produced. Ethylene oxide 5.3 g was added to this solution and agitated at room temperature and 1 atom. After reacting for 2 days, a small amount of water was added and the reaction was stopped; then the reaction solution was poured into ether and the polymer produced was precipitated. The precipitate attained was refined by freeze drying from benzene. The yield was 3.5 g (63%). The polymer attained through gel permeation chromatography was mono-modal, the number average molecular weight of the polymer was 1800 (FIG. 5).

Figure 4:
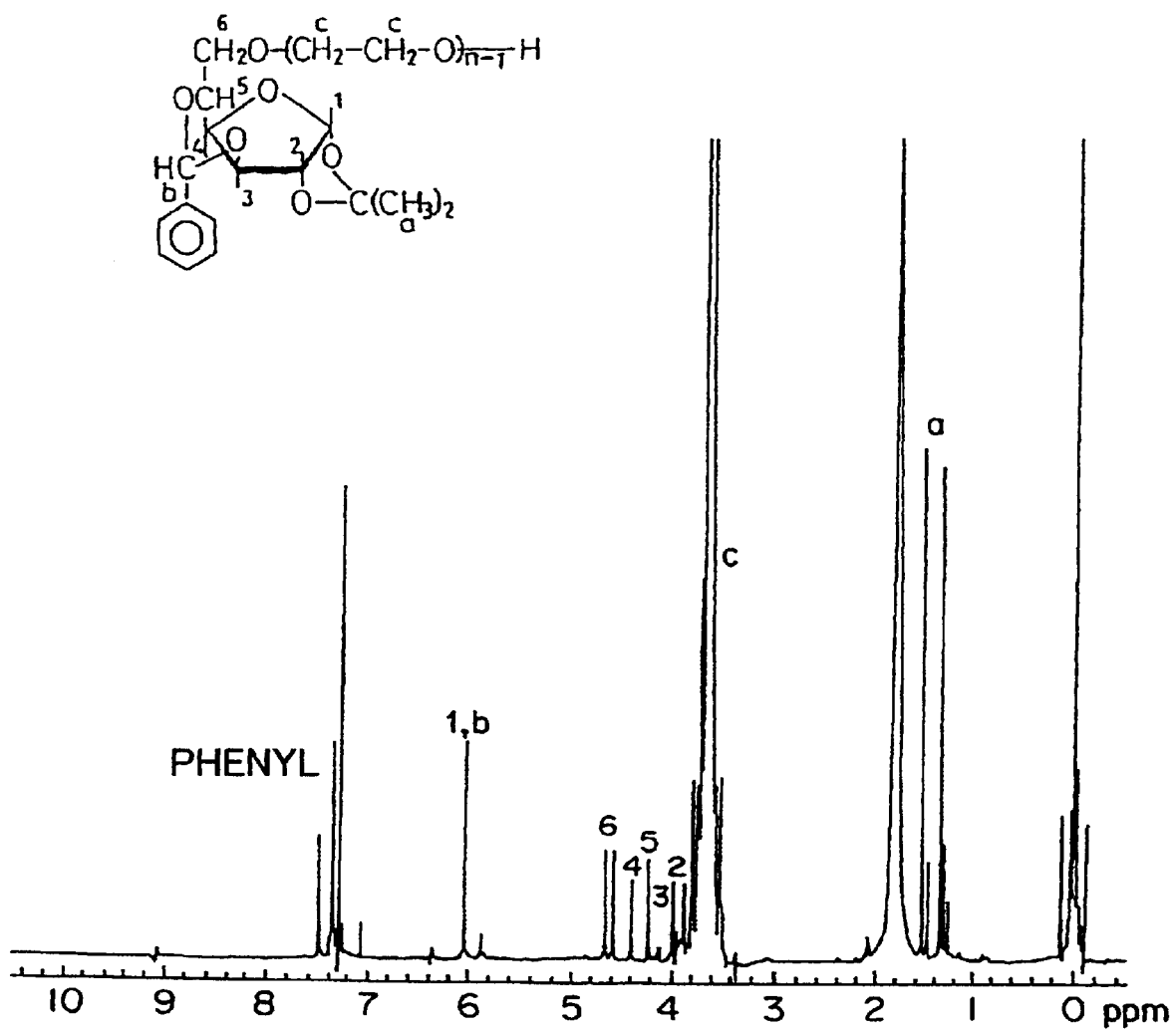
FIG. 4 shows proton nuclear magnetic resonance spectra of the heterotelechelic polyethyleneoxide (the sample of Example 2 mentioned later) which quantitatively has a 3,5-O-benzylidene-1,2-O-isopropylidene-D-glucofuranose residue at α-terminal and a hydroxy group at ω-terminal p

According to the proton nuclear magnetic resonance spectra in the chloroform deuteride of the polymer attained, this polymer was confirmed to be heterotelechelic oligomer quantitatively having the 3, 5-O-benzylidene-1, 2-O-isopropylidene-D-glucofuranose group on the α-terminal and hydroxy group on the ω-terminal and having the polyethylene oxide (PEO) (FIG. 4). The number average molecular weight of the block polymer determined by the integral ratio of the spectra was 2000.

EXAMPLE 3: Preparation of 1, 2; 3, 4-di-O-isopropylidene-D-galactopyranose-6-O-polyethylene Oxide

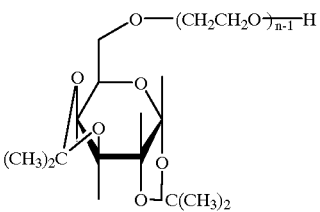

(1) Galactose 50 g was dissolved in acetone 1 liter; copper sulfuric anhydride 100 g and concentrated sulfuric acid 5 ml were added and this was agitated and reacted for 24 hours at room temperature. After the reaction was completed, the unreacted material was filtered out and the filtered solution was neutralized with calcium hydroxide aqueous solution. The unnecessary salt was filtered out, then the solvent was removed under vacuum and vacuum distilled; the 1, 2; 3, 4-di-O-isopropylidene-D-galactopyranose shown in the following formula was attained. The yield was 35 g (48%).

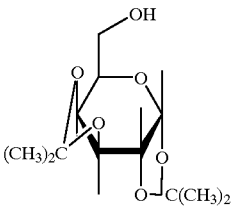

The above compound 180 mg, THF 15 ml, and potassium naphthalene 0.5 mol/L tetrahydrofuran solution 2 ml were added to the reaction container and agitated for 3 minutes in an argon atmosphere; the 6-O-potassium-1, 2; 3, 4-di-O-isopropylidene-D-galactopyranose was produced. Ethylene oxide 4.4 g was added to this solution and agitated at room temperature and 1 atm. After reacting for 2 days, a small amount of water was added and the reaction was stopped; then the reaction solution was poured into ether and the polymer produced was precipitated. The precipitate attained was refined by freeze drying from benzene. The yield was 1.7 g (38%). The polymer attained through gel permeation chromatography was mono-modal, the number average molecular weight of the polymer was 3500 (FIG. 5).

Figure 6:
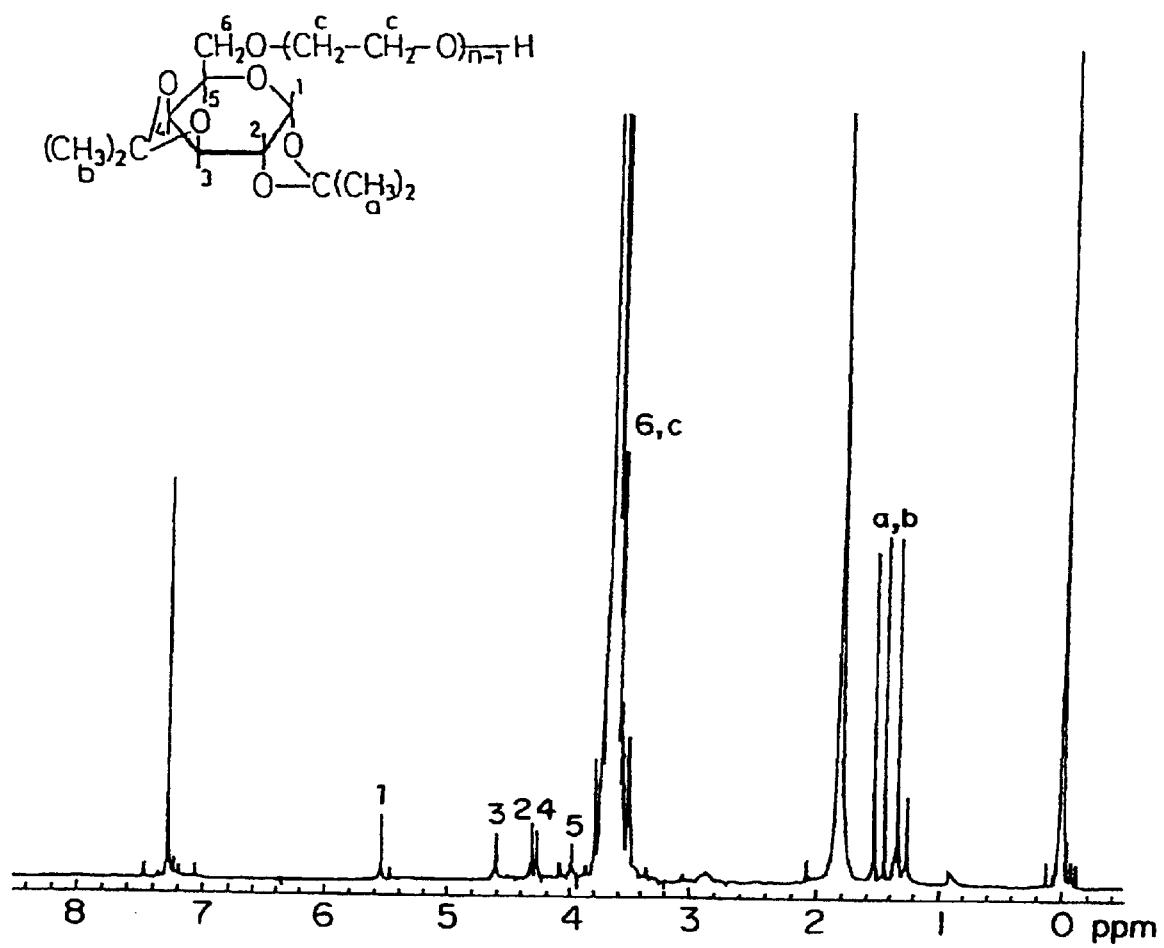
FIG. 6 shows proton nuclear magnetic resonance spectra of the heterotelechelic polyethylene-oxide (the sample of Example 3 mentioned later) which quantitatively has a 1,2;3,4-di-O-isopropylidene-D-galactopyranose residue at α-terminal and a hydroxy group at ω-terminal.

According to the proton nuclear magnetic resonance spectra in the chloroform deuteride of the polymer attained, this polymer was confirmed to be the heterotelechelic oligomer quantitatively having the 1, 2; 3, 4-di-O-isopropylidene-D-galactopyranose group on the α-terminal and hydroxy group on the ω-terminal and having the polyethylene oxide (PEO) (FIG. 6). The number average molecular weight of the polymer determined by the integral ratio of the spectra was 3300.

EXAMPLE 4: Preparation of the Compound Represented by the Following Formula

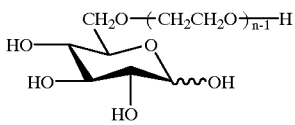

Figure 7:
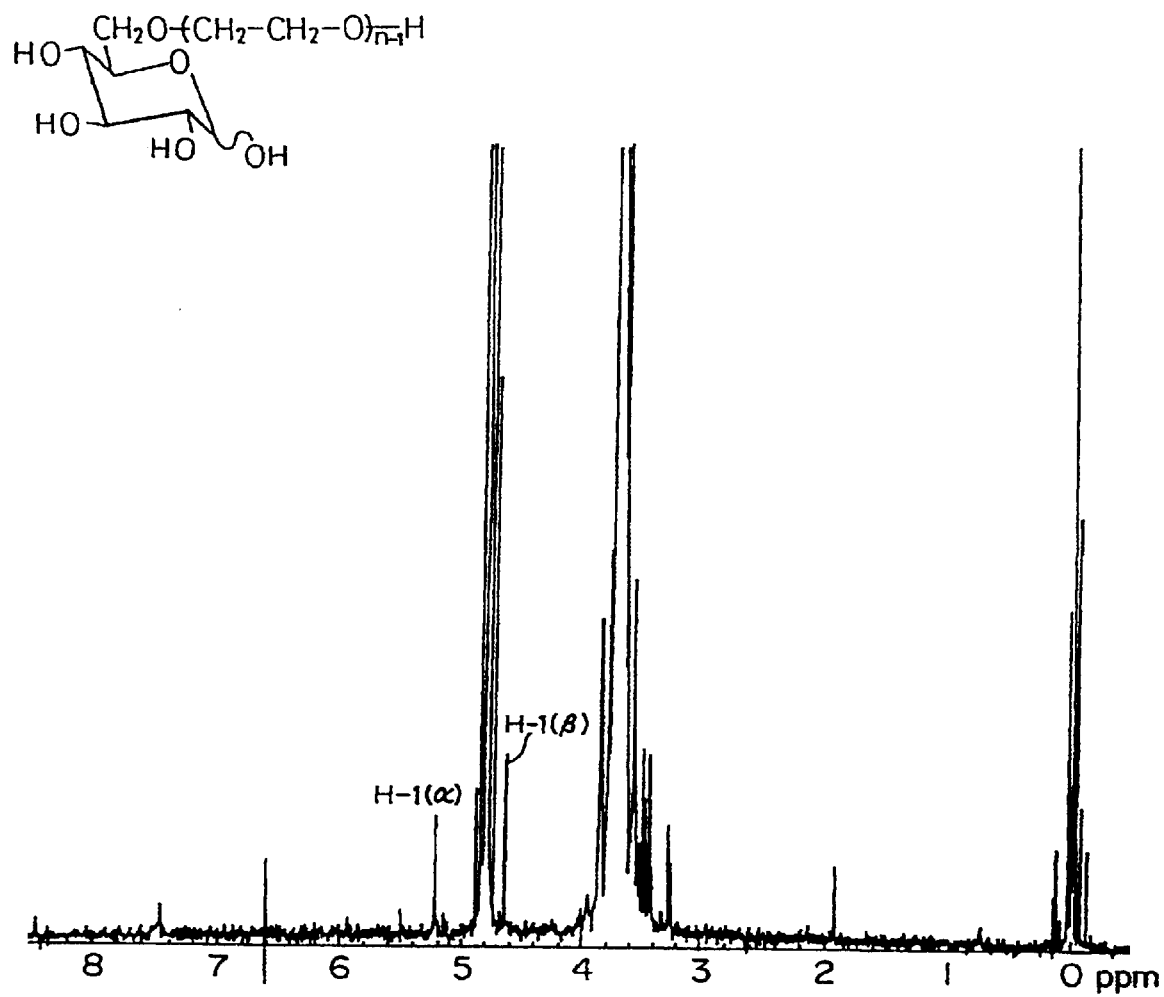
FIG. 7 shows proton nuclear magnetic resonance spectra of glucose (the sample of Example 4 mentioned later) which quantitatively has a polyethyleneoxide chain at the hydroxyl group on the 6-position.

The polyethylene oxide derivative 50 mg attained in Example 2 was dissolved in 90 vol % trifluoroacetate and left standing 40 minutes at room temperature. After the reaction, the solvent was vacuum distilled and refined with gel filtration. The yield was 47 mg (94%). According to the proton nuclear magnetic resonance spectra in the chloroform deuteride of the polymer attained, this polymer was confirmed to be glucose having a polyethylene oxide chain quantitatively on the 6-position hydroxyl group, in which the peak of the benzylidene of the sugar group and the isopropylidene protective group disappeared completely, and which maintains the polyethylene oxide (PEO) unit (FIG. 7).

EXAMPLE 5: Preparation of the Compound Represented by the Following Formula

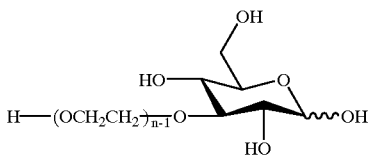

The polyethylene oxide derivative 50 mg attained in Example 1 was dissolved in 90 vol % trifluoroacetate and left standing 40 minutes at room temperature. After the reaction, the solvent was vacuum distilled and refined with gel filtration. The yield was 40 mg (80%). According to the proton nuclear magnetic resonance spectra in the chloroform deuteride of the polymer attained, this polymer was confirmed to be glucose having a polyethylene oxide chain quantitatively on the 3-position hydroxyl group, in which the peak of the two isopropylidene protective groups of the sugar group disappeared completely, and which maintains the polyethylene oxide (PEO) unit.

EXAMPLE 6: Preparation of the Compound Represented by the Following Formula

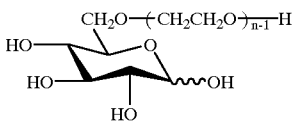

The polyethylene oxide derivative 50 mg attained in Example 3 was dissolved in 90 vol % trifluoroacetate and left standing 40 minutes at room temperature. After the reaction, the solvent was vacuum distilled and refined with gel filtration. The yield was 45 mg (90%). According to the proton nuclear magnetic resonance spectra in the chloroform deuteride of the polymer attained, this polymer was confirmed to be glucose having a polyethylene oxide chain quantitatively on the 6-position hydroxyl group, in which the peak of the isopropylidene protective group and the benzylidene group of the sugar group disappeared completely, and which maintains the polyethylene oxide (PEO) unit.

EXAMPLE 7: Preparation of the Compound Represented by the Following Formula

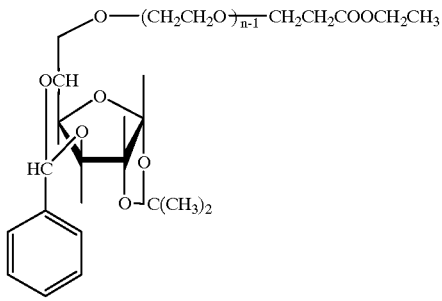

The compound 308 mg, THF 20 ml, and potassium naphthalene 0.5 mol/L tetrahydrofuran solution 2 ml were added to the reaction container and agitated 3 minutes in an argon atmosphere; 6-O-potassium-3, 5-O-benzylidene-1, 2-O-isopropylidene-D-glucofuranose was produced. Ethylene oxide 5.3 g was added to this solution and agitated for 2 days at room temperature and 1 atm. Dimethylsulfoxide solution 10 ml including ethyl 2-bromopropionate acid ethyl 0.2 g was added to this reaction solution and this underwent chemical modification in the reaction for 24 hours at room temperature. This solution was poured into ether and the polymer produced was precipitated. The precipitate attained was refined by freeze drying from benzene. The yield was 3.0 g (48%). The polymer attained through gel permeation chromatography was mono-modal, the number average molecular weight of the polymer was 2000.

According to the proton nuclear magnetic resonance spectra in the chloroform deuteride of the polymer attained, it was confirmed to be a heterotelechelic oligomer quantitatively having 3, 5-O-benzylidene-1, 2-O-isopropylidene-D-glucofuranose group on the sugar residue and 3-ethoxyoxopropyl group on the ω-terminal, and in which a new peak based on the ethylester propionate introduced was shown (1.2, 2.3 ppm) in addition to the peak (3.6 ppm (PEO): 1.2, 1.5 ppm (isopropylidene), 3.8, 4.0, 4.2, 4.4, 4.5, 4.6, 6.0 ppm (glucofuranose) based on the polyoxyethylene chain and 3, 5-O-benzylidene-1, 2-O-isopropylidene-D-glucofuranose group.

EXAMPLE 8: Preparation of the Compound Represented by the Following Formula

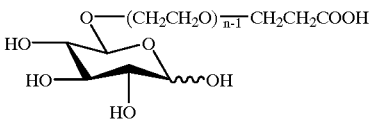

The polyethylene oxide derivative 50 mg attained in Example 7 was dissolved in 90 vol % trifluoracetate and left standing 40 minutes at room temperature. After the reaction, the solvent was vacuum distilled and refined with gel filtration. The yield was 43 mg (86%). According to the proton nuclear magnetic resonance spectra in the chloroform deuteride of the polymer attained, this polymer was confirmed to be a heterotelechelic oligomer having a glucose group bonded at the 6-position on the α-terminal and a 3-carboxyethyl group on the ω-terminal, in which the peak of the ethyl ester and the peak of the isopropylidene protective group and the benzylidene protective group of the sugar group had completely disappeared, and which maintains the unit of polyethylene oxide (PEO).

EXAMPLE 9: Preparation of the Compound Represented by the Following Formula

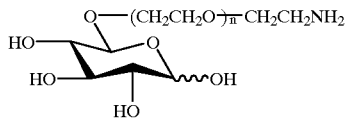

(1) The compound obtained in step (1) of Example 2 308 mg, THF 20 ml, and potassium naphthalene 0.5 mol/L-tetrahydrofuran solution 2 ml were added to the reaction container and agitated for 3 minutes in an argon atmosphere; 6-O-potassium-3, 5-O-benzylidene-1, 2-O-isopropylidene-D-glucofuranose was produced. Ethylene oxide 5.3 g was added to this solution and agitated for 2 days at room temperature and 1 atm. A dimethylsulfoxide solution 10 ml including N-(2-bromoethyl)phthalimide 0.4 g was added to this reaction solution, reacted 24 hours at room temperature, and underwent chemical modification. This solution was poured into ether and the polymer produced was precipitated. The precipitate attained was refined by freeze drying from benzene.

(2) The polyethylene oxide derivative 50 mg attained was dissolved in 90 vol % trifluoroacetate and left standing 40 minutes at room temperature. After the reaction, the solvent was vacuum distilled and refined with gel filtration. The yield was 40 mg (80%). According to the proton nuclear magnetic resonance spectra in the chloroform deuteride of the polymer attained, this polymer maintained the polyethylene oxide (PEO) unit, the peaks of the isopropylidene protective group and the benzylidene protective group of the sugar group disappeared completely, and a new peak based on aminoethyl group was shown (2.75, 3.06 ppm), and, thus, it was confirmed to be a heterotelechelic oligomer having a glucose group bonded in the 6-position on the α-terminal and the 2-aminoethyl group on the ω-terminal.

EXAMPLE 10: Preparation of the Compound Represented by the Following Formula

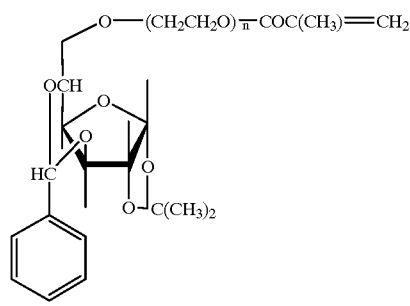

A reactor was charged with 308 mg of a compound obtained in the same manner as in Step (1) of Example 2, 20 ml of THF and 2 ml of 0.5 mol/L-tetra-hydrofuran solution of naphthalene potassium, and the resulting solution was stirred for three minutes in the atmosphere of argon, and, thus, there was formed 6-potassium-3, 5-O-benzylidene-1, 2-O-isopropylidene-D-glucofuranose. There was added 5.3 g of ethylene oxide to this solution, which was then stirred at a room temperature under 1 atm. After two day's reaction, 2.0 g of methacrylic acid anhydride was added, and the solution was further subjected to reaction for 48 hours at a room temperature. Then, the reaction liquid was poured into ether so that formed polymer might be precipitated. The obtained precipitate was purified by means of freeze drying from benzene. The yield was 4.2 g (75%). The polymer obtained by means of gel permeation chromatography was mono-modal and had a number average molecular weight of 1800.

Proton nuclear magnetic resonance spectra of the obtained polymer in chloroform deuteride taught that this polymer was a heterotelechelic oligomer which quantitatively had a unit of polyethylene oxide (PEO), had a 3, 5-O-benzylidene-1, 2-O-isopropylidene-D-glucofuranose residue at α-terminal, and had a methacryloyl group at ω-terminal. As for the introduction of methacryloyl group, it was confirmed also from the observation of the absorption of ester carbonyl near 1700 cm$^{-1}$ in infrared absorption spectrum.

NMR spectrum (δ, ppm); 1.3 (s), 1.5 (s), 1.9 (s), 3.7 (s), 3.9 (s), 4.0 (s), 4.2 (s), 4.4 (s), 4.6 (d), 5.6 (s)

EXAMPLE 11: Preparation of the Compound Represented by the Following Formula

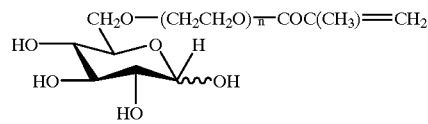

There was dissolved 50 mg of polyethylene oxide obtained in Example 10 into 97 vol % acetic acid, and the resulting solution was left still for 40 minutes at a room temperature. After reaction was over, the solvent was distilled off, and the solution was purified by gel filtration. The yield was 45 mg (90%). Proton nuclear magnetic resonance spectra of the obtained polymer in chloroform deuteride taught that this polymer was a glucose which had a unit of polyethylene oxide (PEO), and in which the peaks of benzylidene- and isopropylidene-protecting groups of sugar residue had completely disappeared, and which quantitatively had polyethylene oxide chain at the hydroxyl group of 6-position. As for the remaining of methacryloyl group, it was confirmed also from the observation of the absorption of ester carbonyl near 1700 cm$^{-1}$ in infrared absorption spectrum.

NMR spectrum (δ, ppm); 1.9 (s), 3.7 (s), 4.6 (s) (β), 4.8 (s), 5.2 (s) (α), 5.6 (s), 6.2 (s)

EXAMPLE 12: Preparation of the Compound Represented by the Following Formula

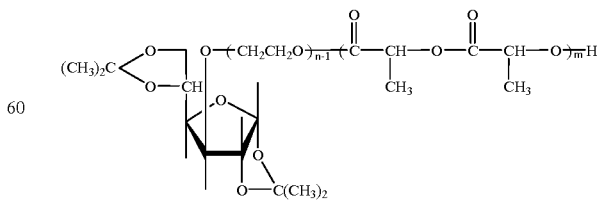

A reactor was charged with 130 mg of the compound obtained in Step (1) of Example 1, 20 ml of THF and 1 ml of 0.5 mol/L-tetrahydrofuran solution of naphthalene potassium, and the resulting solution was stirred for three minutes in the atmosphere of argon, and, thus, there was formed 3-O-potassium-1, 2; 5, 6-di-O-isopropylidene-D-glucofuranose. There was added 3.1 g of ethylene oxide to this solution, which was then stirred at a room temperature under 1 atm. After two day's reaction, 20 ml of a solution of L-lactide dissolved in THF (2 mol/L) was added, and the resulting solution was stirred for one hour at a room temperature so that it might be polymerized. After the reaction was over, the reaction liquid was poured into 15 l of 2-propanol so that formed polymer might be precipitated. After recovered by centrifugation, the obtained polymer was purified by means of freeze drying from benzene. The yield was 7.6 g (85.8%). The polymer obtained by means of gel permeation chromatography was mono-modal and had a number average molecular weight of 19,000.

Proton nuclear magnetic resonance spectra of the obtained polymer in chloroform deuteride taught that this polymer was a block polymer having both segments of polyethylene oxide (PEO) and polylactide (PLA), which polymer quantitatively had a 1, 2; 5, 6-di-O-isopropylidene-D-glucofuranose residue at α-terminal and a hydroxyl group at ω-terminal. The segment length of PEO and PLA were respectively 6300 and 12,900 in number average molecular weight.

NMR spectrum (δ, ppm); 1.3 (d), 1.5 (d), 1.6 (s), 3 3.6 (s), 3.9 (s), 4.0 (s), 4.1 (s), 4.2 (s), 4.6 (s), 5.2 (s), 5.8 (s)

EXAMPLE 13: Preparation of the Compound Represented by the Following Formula

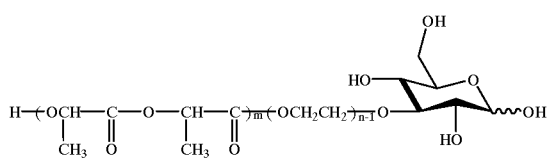

There was dissolved 40 mg of the block polymer obtained in Example 12 into 2 ml of an 8:2 (v/v) trifluoroacetic acid-water solution, and the resulting solution was stirred for one hour at a room temperature.

The reaction aqueous solution was added dropwise to 20 ml of 2-propanol at −20° C. so that polymer might be precipitated. After centrifugation, polymer was purified by means of drying under a reduced pressure. The yield was 31.1 mg (78.0%). As for the number average molecular weight of the recovered polymer, it was found by means of gel permeation chromatography and NMR that the segment length of PEO and PLA were respectively 6300 and 11,500, and that the main chain had hardly been severed by the treatment with 80% trifluoroacetic acid. It was found by means of NMR, on the other hand, that the signal of isopropylidene which was a protecting group of sugar residue had disappeared, and, instead, a signal of anomeric proton of reducing sugar was observed, and quantitative de-protection was confirmed.

NMR spectrum (δ, ppm); 1.6 (s), 3.6 (s), 4–5 (m), 5.2 (s), 6.1 (s) (β), 6.4 (s) (α)

EXAMPLE 14: Preparation of High-Molecular Micelle

There was dissolved 100 mg of the polymer obtained in Example 12 into 20 ml of dimethyl acetamide, and the resulting solution was dialyzed against water for 24 hours with use of a dialysis tube having a differential molecular weight of 12,000–14,000 (water was replaced after 3, 6 and 9 hours). When this solution was analyzed with dynamic light scattering, there was confirmed the formation of micelle having an average particle size of 40 nm. The critical micelle concentration of this high-molecular micelle was 5 mg/l.

EXAMPLE 15: Preparation of High-Molecular Micelle

High-molecular micelle was prepared from the polymer obtained in Example 13, in the same manner as in Example 14, and, thus, there was produced stable micelle having an average particle size of 40 nm and a critical micelle concentration of 5 mg/l.

Industrial applicability:

This invention provides a mono-modal heterotelechelic oligomer or polymer which has a polyethylene oxide segment or both a polyethylene oxide segment and a polyester segment, and which has a sugar residue at one terminal of the segment and a different functional group at the other terminal. It is foreseen, from its constituent components, that the above oligomer or polymer will show excellent bioavailability. Moreover, owing to the different functional groups at the both terminals, said oligomer or polymer is expected to be used, per se or with use of the functional groups at the both terminals, as a carrier for medicine or other active materials. This invention has therefore availability in the field of production of oligomer or polymer, medicines and diagnostic reagents.

We claim:

1. A polyethylene oxide derivative which is represented by the following formula (I):

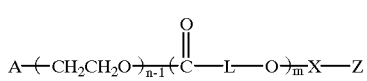

wherein A denotes a sugar residue represented by the following formula

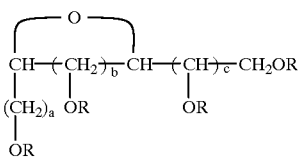

wherein one R denotes a covalent bond with the adjacent methylene group in formula (I); and the other R groups denote hydrogen atom, $C_{1-5}$ alkyl, $C_{1-5}$ alkylcarbonyl or tri-$C_{1-5}$ alkylsilyl wherein the alkyl groups are the same or different or, optionally, two of said R groups in combination, while forming an acetal together with the oxygen atom to which the Rs are bound, denote $C_{3-5}$ alkylidene or benzylidene whose methine may be substituted with $C_{1-3}$ alkyl; a denotes an integer of 0 or 1, b denotes an integer of 2 or 3, and c denotes an integer of 0 or 1, n denotes an integer of 5–10,000, L denotes a linkage group represented by the following formula

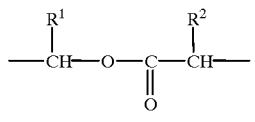

or

wherein $R^1$ and $R^2$ independently denote hydrogen atom, $C_{1-6}$ alkyl, aryl or $C_{1-3}$ alkylaryl, m denotes an integer of 0 or 2–10,000, X denotes a single bond or —$CH_2CH_2$—, and when X is a single bond, Z denotes hydrogen atom, alkali metal, acryloyl, methacryloyl, cinnamoyl, p-toluenesulfonyl, allyl, carboxymethyl, carboxyethyl, ethoxycarbonylmethyl, ethoxycarbonylethyl, 2-aminoethyl, 3-aminopropyl, 4-aminobutyl, vinylbenzyl, di-$C_{1-5}$ alkyloxy-$C_{2-3}$ alkyl or aldehyde-$C_{2-3}$ alkyl, while, when X is —$CH_2CH_2$— and m is 0, Z denotes hydroxyl, mercapto, amino or halogen atom.

2. The polyethylene oxide derivative of claim 1 wherein m denotes 0 (zero).

3. The polyethylene oxide derivative of claim 1 wherein m denotes an integer of 2–10,000.

4. The polyethylene oxide derivative of claim 1 wherein the sugar residue A is derived by removing a hydrogen atom from one of the R positions of a monosaccharide selected from the group consisting of glucose, galactose, mannose, fructose, ribose and xylose.

5. The polyethylene oxide derivative of claim 1 wherein the groups R other than the linkage of the sugar residue to the remainder of formula (I) each denote a hydrogen atom.

6. The polyethylene oxide derivative of claim 1 wherein two R groups other than the linkage of the sugar residue to the remainder of formula (I) form, in combination, one or two linkages selected from the group consisting of isopropylidene, benzylidene, 1-butylidene, 2-butylidene, 3-pentylidene and methyl benzylidene.

7. The polyethylene oxide derivative of claim 1 wherein n denotes an integer of 10–200.

8. The polyethylene oxide derivative of claim 1 wherein X is a single bond and Z denotes a hydrogen atom or potassium.

9. The polyethylene oxide derivative of claim 1 wherein X is a single bond and Z denotes acryloyl, methacryloyl or p-toluene sulfonyl.

10. The polyethylene oxide derivative of claim 1 wherein X is a single bond and Z denotes allyl, carboxymethyl, carboxyethyl, ethoxycarbonylmethyl, ethoxycarbonylethyl, 2-aminoethyl or vinylbenzyl.

11. The polyethylene oxide derivative of claim 1 wherein X is —$CH_2CH_2$—, m is 0 and Z denotes mercapto, chlorine, bromine or iodine.

12. The polyethylene oxide derivative of claim 1 wherein the sugar residue A is derived by removing a hydrogen atom from one of the R positions of glucose or glactose, the groups R other than the linkage of the sugar residue to the remainder of formula (I) are either a hydrogen atom or form one or two isopropylidene and benzylidene linkages, n denotes an integer of 10–200, m denotes an integer of 5–200, L represents a formula

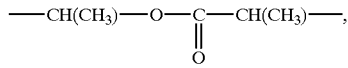

and Z denotes a hydrogen atom, potassium ion, acryloyl, methacryloyl or p-toluene sulfonyl, allyl, carboxymethyl, carboxyethyl, ethoxycarbonylmethyl, ethoxycarbonylethyl or vinylbenzyl.

13. A process to produce a polyethylene oxide derivative of claim 1 which process comprises the following steps:

Step (1): polymerizing ethylene oxide in the presence of a polymerization initiator represented by the following formula (II)

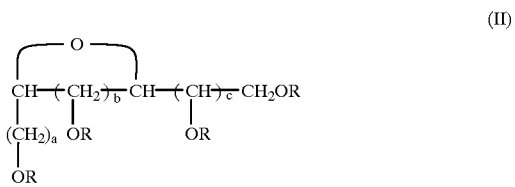

wherein one R denotes an alkali metal (M); and the other R groups optionally denote $C_{1-5}$ alkyl, $C_{1-5}$ alkylcarbonyl or tri-$C_{1-5}$ alkylsilyl wherein the alkyl groups are the same or different or, optionally, two of said R groups in combination, while forming an acetal together with the oxygen atom to which the Rs are bound, denote $C_{3-5}$ alkylidene or benzylidene whose methine may be substituted with $C_{1-3}$ alkyl; a denotes an integer of 0 or 1, b denotes an integer of 2 or 3, and c denotes an integer of 0 or 1;

Step (2): optionally, (i) hydrolyzina the oligomer or polymer obtained in the above Step (1) represented by the following formula (III)

wherein A and n are as defined in formula (I)

or (ii) reacting said oligomer or polymer with

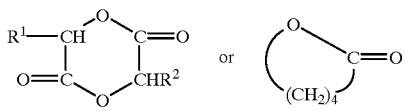

wherein $R^1$ and $R^2$ are as defined in formula (I) to form an oligomer or polymer represented by the following formula (IV)

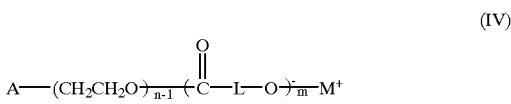

wherein A, L, m and n are as defined in formula (I);

Step (3): optionally, reacting the oligomer or polymer obtained in Step (1) or Step (2) either with
(i) acrylic acid, methacrylic acid, or p-toluenesulfonic acid or with
(ii) the halide represented by the following formula (V)

halo-E       (V)

wherein halo denotes chlorine, bromine or iodine, and E denotes allyl, carboxymethyl, ethoxycarbonylmethyl, ethoxycarbonylethyl, vinylbenzyl, N-phthalimide ethyl, N-phthalimide propyl or N-phthalimide butyl;

Step (4): optionally eliminating groups R of the sugar residue A except the above-mentioned linkage.

* * * * *

UNITED STATES PATENT AND TRADEMARK OFFICE
CERTIFICATE OF CORRECTION

PATENT NO. : 5,973,069
DATED : October 26, 1999
INVENTOR(S) : Kazonori Katoaka, et al.

It is certified that error appears in the above-identified patent and that said Letters Patent is hereby corrected as shown below:

Column 5, Lines 11 and 12: After "terminal p", FIG. 5 should begin a new paragraph.

Column 5, Line 19: "polyethylene-oxide" should read --polyethyleneoxide--

Column 10, Line 18: "Cl" should read --C$\ell$--

Column 16, Line 54: "as" should read --was--

Column 16, Line 64: "1 2" should read --1,2--

Signed and Sealed this

Twenty-third Day of January, 2001

Attest:

Q. TODD DICKINSON

*Attesting Officer*  *Commissioner of Patents and Trademarks*